United States Patent [19]

Gaginella et al.

[11] Patent Number: 5,112,856

[45] Date of Patent: May 12, 1992

[54] THERAPEUTIC TREATMENT OF INTESTINAL INFLAMMATION BY ADMINISTRATION OF 3,4-DIHYDRO-2H-1-BENZOPYRAN DERIVATIVES

[75] Inventors: Timothy S. Gaginella, Wayne; Ann F. Welton, West Caldwell; Peter C. Will, Nutley, all of N.J.

[73] Assignee: Hoffmann-La Roche Inc., Nutley, N.J.

[21] Appl. No.: 569,241

[22] Filed: Aug. 16, 1990

Related U.S. Application Data

[63] Continuation of Ser. No. 315,014, Feb. 24, 1989, abandoned, which is a continuation of Ser. No. 897,450, Aug. 15, 1986, abandoned.

[51] Int. Cl.[5] ............................................. A61K 31/35
[52] U.S. Cl. ...................................................... 514/456
[58] Field of Search ........................................ 514/456

[56] References Cited

U.S. PATENT DOCUMENTS 4,885,309  12/1989  Welton ................................ 514/456

OTHER PUBLICATIONS

Prog. Drug Res., 28, 214, 261–267 (1984).
Pathology, rubin. E. and Farber, J., pp. 648–655 (1988).
Pathology, Rubin, E. and Farber, J., pp. 648–655 (1988).

*Primary Examiner*—Stanley J. Friedman
*Attorney, Agent, or Firm*—George M. Gould; George W. Johnston; Alan P. Kass

[57] ABSTRACT

Inflammatory bowel disease and other leukotriene-mediated inflammation of the intestinal mucosa are treated therapeutically by the oral, rectal or parenteral administration of racemic-6-acetyl-7-[5-(4-acetyl-3-hydroxy-2-propylphenoxy)pentyloxy]-3,4-dihydro-2H-1-benzopyran-2-carboxylic acid, or a salt, lower alkyl ester or enantiomer thereof.

19 Claims, 5 Drawing Sheets

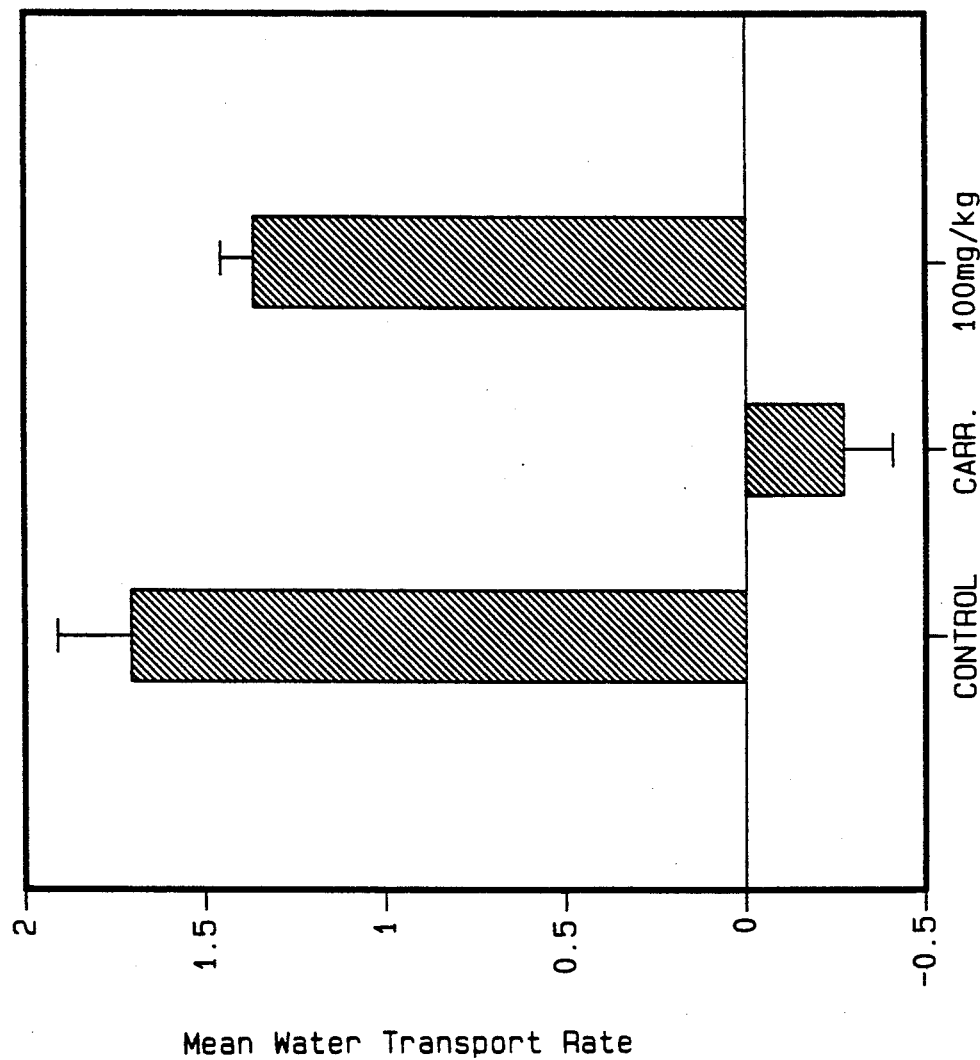

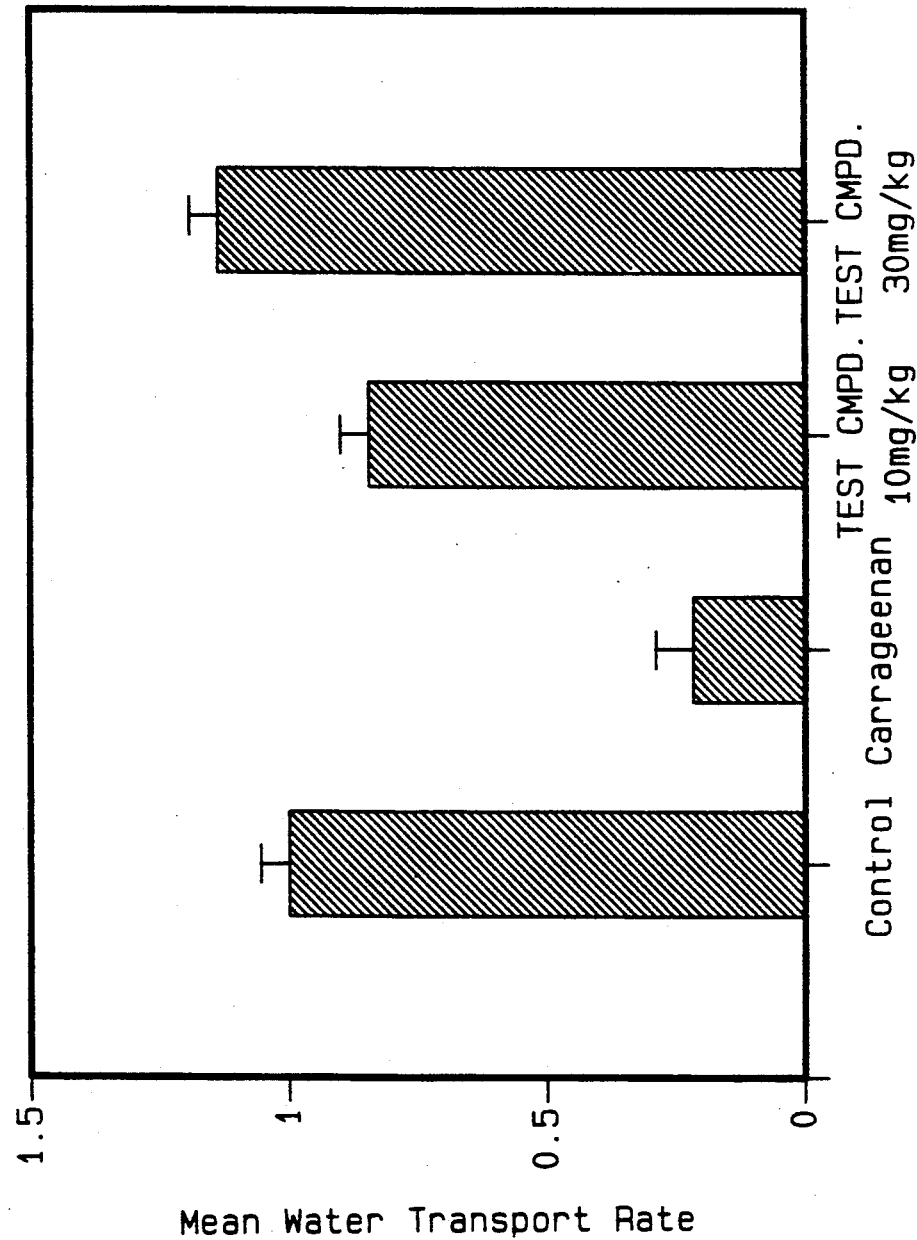

THERAPEUTIC TREATMENT OF INTESTINAL INFLAMMATION BY ADMINISTRATION OF 3,4-DIHYDRO-2H-1-BENZOPYRAN DERIVATIVES

This application is a continuation of application Ser. No. 07/315,014, filed Feb. 24, 1989, which is a Rule 60 continuation of Ser. No. 06/897,450, filed Aug. 15, 1986 both are abandoned.

BACKGROUND OF THE INVENTION

The present invention relates to the use of racemic 6-acetyl-7-[5-(4-acetyl-3-hydroxy-2-propylphenoxy)-pentyloxy]-3,4-dihydro-2H-1-benzopyran-2-carboxylic acid, or a salt, lower alkyl ester or enantiomer thereof, as an anti-inflammatory agent in the therapeutic treatment of inflammatory bowel disease and other leukotriene-mediated mucosal inflammation of the intestines, by various routes of administration.

Inflammatory bowel disease is a term often used to refer to inflammatory conditions of the bowel or other portions of the intestinal tract which have as a common feature a chronic or acute inflammation of the gastrointestinal mucosa. Various forms are generally understood to include Crohn's disease of the ileum and colon, ulcerative colitis, neonatal necrotizing enterocolitis and food allergy. They are characterized histopathologically by ulceration, pseudomembranes, radiologically visible lesions, edema and the build-up of inflammatory cells, and symptoms involve diarrhea, abdominal pain, weight loss and hypoproteinemia. Descriptions in the literature include Northfield, *Drugs* 14: 198-206 (1977); Blaker, et al. Eur. J. Pediatr. 139: 162-164 (1982); Singleton, The Gastroenterology Annual, pp. 268-310 (1983); Saco, et al. J. Amer. Acad. Dermatol. 4: 619-629 (1981); Prantera, et al. Ital. J. Gastroenterol. 13: 24-27 (1981); Sales, et al. Arch. Int. Med. 143: 294-299 (1983), and Ament, Inflammatory Bowel Diseases, Martinus Nijhoff Publ., Boston, Mass., pp. 254-268 (1982). Less frequent but also possible are mucosal inflammation of other sections of the gastrointestinal tract, such as duodenitis, jejunitis and proctitis.

Drugs useful in the treatment of such conditions include sulfasalazine and others that deliver 5-aminosalicylate to the bowel, corticosteroids, metronidazole and cholestyramine, as described by Sack and Peppercorn in Pharmacotherapy 3: 158-176 (1983).

SUMMARY OF THE INVENTION

The present invention concerns, in one of its aspects, a method for treating inflammatory bowel disease and other leukotriene-mediated mucosal inflammation of the intestines, chiefly the small and large intestines, by the administration of an effective anti-inflammatory amount of reacemic 6-acetyl-7-[5-(4-acetyl-3-hydroxy-2-propylphenoxy)pentyloxy]-3,4-dihydro-2H-1-benzopyran-2-carboxylic acid, or an alkyl ester, enantiomer or salt thereof. Several routes of administration are possible, preferably oral, but also including rectal and parenteral. The invention also includes, as another aspect, pharmaceutical compositions useful in the practice of this method, which contain the above mentioned compound as the active ingredient and are prepared as an oral dosage form for release of the active ingredient in the small and large intestines, or as a rectal dosage form, or as a parenteral dosage form.

The compounds and compositions of this invention can be used to effectively treat mucosal inflammation of the intestine, including inflammatory bowel disease, which appear to be leukotriene mediated. The term "leukotriene-mediated" is used to mean that the substance leukotriene is actively involved in some way in the causation of the inflammatory condition or in the manifestation of its symptoms, or both.

The same compounds involved here have been previously disclosed for other purposes in South African published patent application ZA 8404519 Dec. 24, 1984), and in particular for antiallergic uses, including asthma treatment. Still other dihydrobenzopyran compounds have been described in European patent publications 0139809 (May 8, 1985) and 0150447 (Jun. 7, 1985) as leukotriene inhibitors useful for treating allergies as well as inflammatory conditions such as rheumatoid arthritis. The present invention is based on the discovery that the particular compounds described here are especially useful and exhibit a high degree of potency in counteracting the above mentioned mucosal inflammation.

BRIEF DESCRIPTION OF THE DRAWINGS

FIG. 4—Effect of sulfasalazine on water transport rate in the guinea pig colon, in vivo.

FIG. 5—Effect of test inhibitor on water transport rate in the guinea pig colon, in vivo.

DETAILED DESCRIPTION OF THE INVENTION

Figure 1:
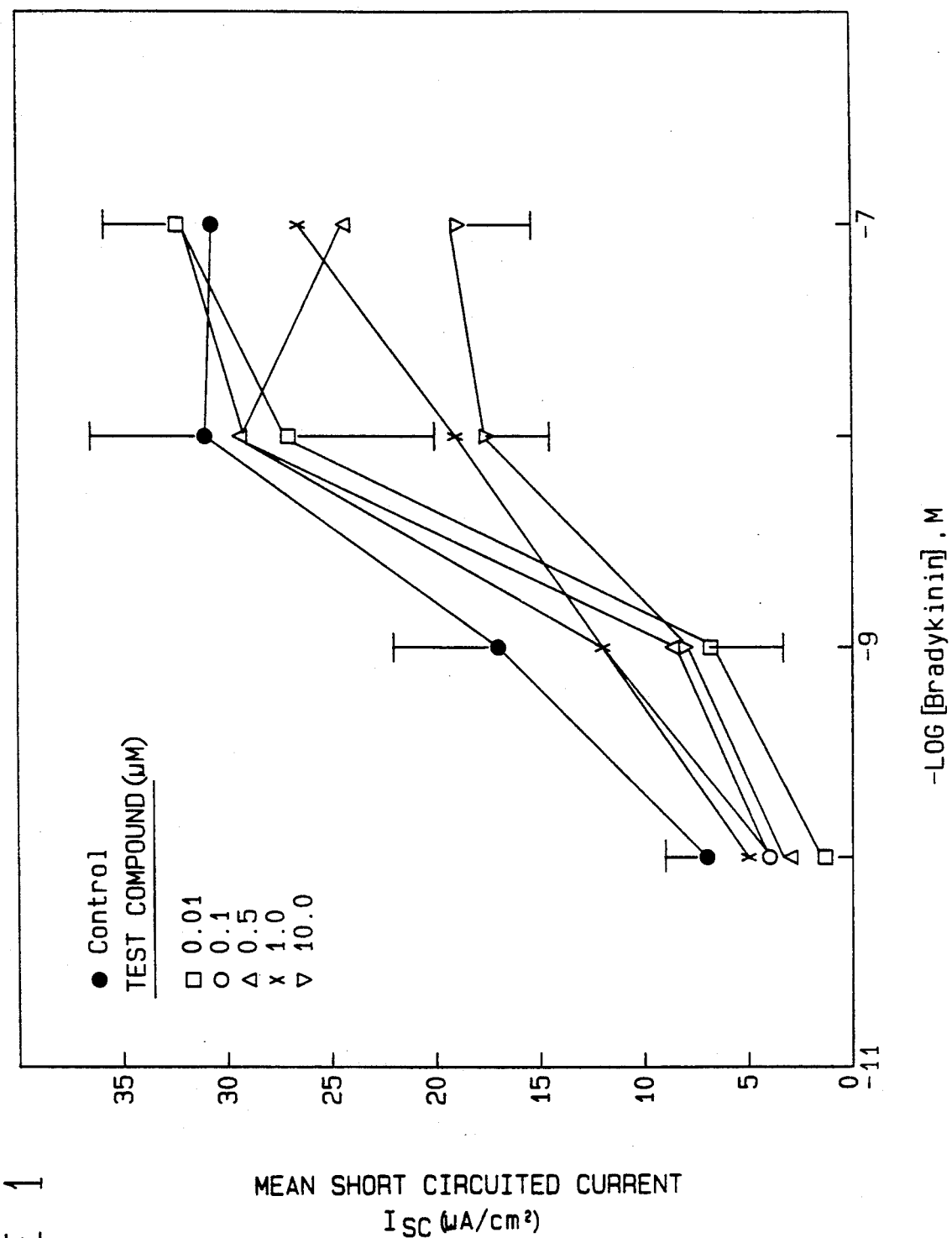
FIG. 1—Effect of test inhibitor to reduce the secretory activity of bradykinin.

The anti-inflammatory compounds useful in the practice of the present invention have the formula

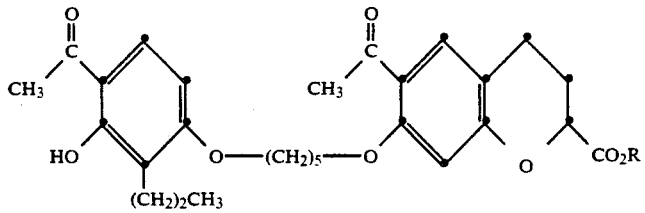

in which R stands for hydrogen or lower alkyl.

The term "lower alkyl" is used in this disclosure to refer to a straight or branched chain saturated hydrocarbon, preferably containing 1 to 7 carbon atoms, for example, methyl, ethyl, propyl, isopropyl, butyl, t-butyl, neopentyl, pentyl, hexyl, heptyl, and the like.

The compound of formula I useful in the practice of this invention can be prepared in accordance with Reaction Scheme I, as follows:

REACTION SCHEME I

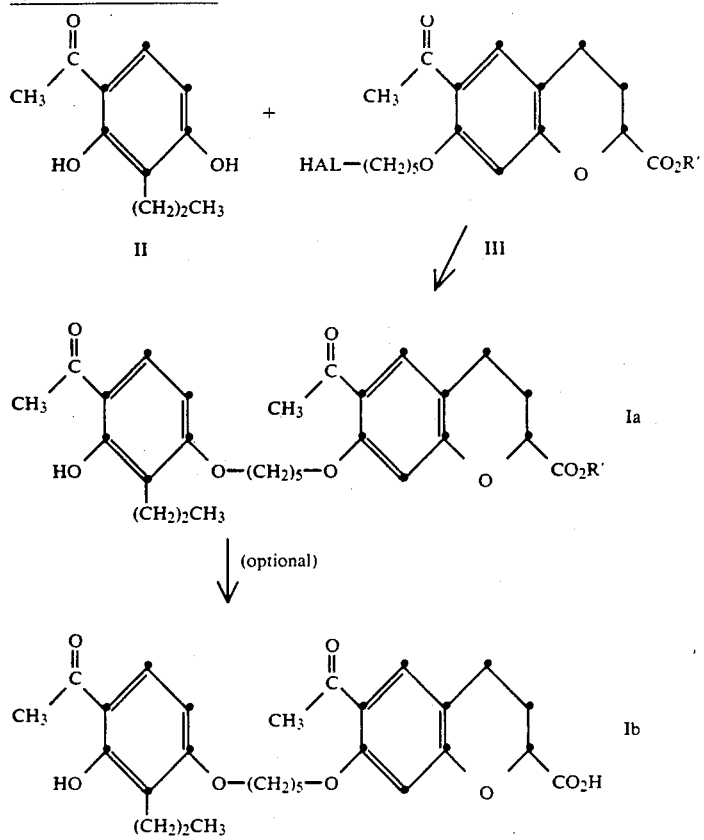

in which R' stands for lower alkyl, which is as defined above for the compound of formula I.

As used throughout this disclosure, the terms "HAL" and "halogen" refer to all the halogens, that is, bromine, chlorine, fluorine and iodine, although among these, bromine, chlorine and iodine are preferred.

In Reaction Scheme I, the reaction of a compound of formula II, which is a known compound or can be prepared according to known procedures, with a compound of formula III, to yield the compound of formula Ia, is carried out under anhydrous conditions in an inert solvent, for example, acetone, acetonitrile, methyl ethyl ketone, diethyl ketone, dimethylformamide, or the like. The reaction is conducted at the reflux temperature of the reaction mixture, preferably at a temperature in the range from about 70° to about 100° C., and in the presence of an acid acceptor, such as potassium carbonate, or the like. The preferred solvent is a mixture of acetone and dimethylformamide. The resulting compound of formula Ia can be recovered using conventional methods, for example, crystallization, chromatography, or the like.

If desired, the compound of formula Ia, which itself is useful in the described method of this invention, can be converted to the compound of formula Ib by hydrolysis. The hydrolysis is carried out with an alkali metal hydroxide, for example, lithium hydroxide, sodium hydroxide, potassium hydroxide, or the like, in a mixture of water and a water miscible solvent, for example, methanol, ethanol, tetrahydrofuran, or the like, at a temperature in the range from about room temperature (for example, 20° to 25° C.) to the reflux temperature. The resulting compound of formula Ib of this invention can be recovered by conventional methods, such as extraction, crystallization, chromatography, or the like.

This invention can also be practiced with use of pharmaceutically acceptable salts of the compounds of formula I, when R is hydrogen. These salts can be prepared by reacting an acid of formula I or an enantiomer thereof with a base having a non-toxic, pharmacologically and pharmaceutically acceptable cation. In general, any base which will form a salt with a carboxylic acid and whose pharmacological properties will not cause an adverse physiological effect when absorbed by a warm-blooded animal is considered as being within the scope of the invention. Suitable bases thus include, for example, alkali metal and alkaline earth metal hydroxides or carbonates, such as, sodium hydroxide, potassium hydroxide, calcium hydroxide, potassium carbonate and the like, ammonia, primary, secondary and tertiary amines, such as monoalkylamines, dialkylamines, trialkylamines, nitrogen containing heterocyclic amines, for example, piperidine, basic amino acids such as lysine, and the like. The pharmaceutically acceptable salts thus produced are the functional equivalent of the corresponding 3,4-dihydro-2H-1-benzopyran acid of formula I and its enantiomers and one skilled in the art will appreciate that, to the extent that the salts of the invention are useful in therapy, the variety of salts encompassed by this invention are limited only by the criterion that the bases employed in forming the salts be both non-toxic and physiologically acceptable.

The intermediates of formula III used for the preparation of the compounds of formula I can be prepared according to Reaction Scheme II, as follows:

REACTION SCHEME II

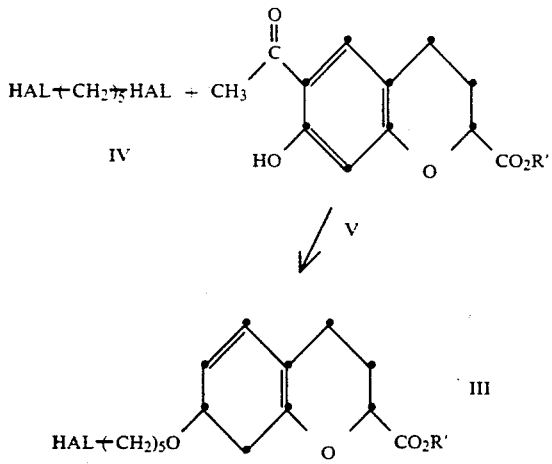

in which HAL and R' are as defined above.

In Reaction Scheme II, the reaction of a compound of formula IV, which itself is a known compound or can be prepared according to known procedures, with a compound of formula V, to yield a compound of formula III, is carried out in an inert organic solvent such as dimethylformamide, acetone, methyl ethyl ketone, acetonitrile, or the like, preferably acetonitrile. The reaction is conducted in the presence of a base, for instance, an alkali metal carbonate such as potassium carbonate, sodium carbonate, or the like, or, alternatively, an alkali metal hydride such as sodium hydride or the like, at a temperature in the range from about 20° to 150° C., preferably room temperature (for example, 20° to 25° C.). The resulting compound of formula III can be recovered utilizing conventional methods, such as crystallization, extraction, chromatography, or the like.

The intermediates of formula V used for the preparation of the compounds of formula III can be prepared according to Reaction Scheme III, as follows:

REACTION SCHEME III

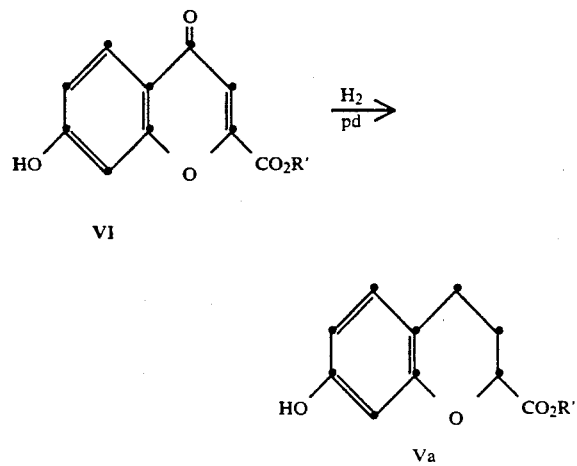

-continued
REACTION SCHEME III

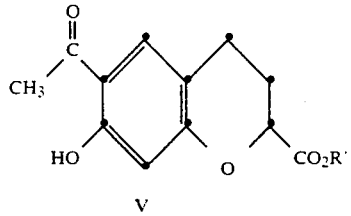

in which R' is as defined above.

In Reaction Scheme III, a compound of formula VI, which are known compounds or can be prepared according to known procedures, is hydrogenated to yield a compound of formula Va. More particularly, the reaction is carried out with a catalyst, for example, palladium on carbon, in a solvent such as a lower carboxylic acid, preferably acetic acid, at a temperature in the range of about 20° C. to about 150° C., preferably at 25° C., and at an increased pressure, preferably 50 psi. The resulting compound of formula Va can be recovered utilizing conventional methods.

The compound of formula Va is then converted to its acyl derivative of formula V utilizing any suitable acylating agent, for example, a lower acyl halide or anhydride, preferred is acetic anhydride, in a suitable base, for example, a lower alkylamine or the like, preferred is pyridine, at a temperature in the range from about 0° C. to about 150° C., preferably at 25° C. The resulting compound of formula V is recovered using conventional methods.

The compounds of formula I possess an asymmetric carbon atom and, therefore, they are ordinarily obtained as racemic mixtures. The resolution of such racemates into the optically active isomers can be carried out by known procedures. Some racemic mixtures can be precipitated as eutectics and can thereafter be separated. Chemical resolution is, however, preferred. By this method, diastereomeric salts are formed from the racemic mixture of a compound of formula I, when R is hydrogen, with an optically active resolving agent, for example, an optically active base, such as d-(+)- or l-(−)-α-methylbenzylamine. The formed diastereomeric salts are separated by selective crystallization and converted to the corresponding optical isomer. Thus, the invention involves the use of racemates of the compounds of formula I, as well as their optically active isomers (enantiomers).

Further details and more specific methods of preparation for the compounds of formula I are found in the aforementioned South African patent publication.

Because of the nature of the condition to be treated, the preferred route of administration for the compounds of formula I is the oral route, which will directly expose the inflamed intestinal tissue surface to the compound. For oral administration these compounds can be administered in the form of tablets, pills, capsules, powder, granules or beads in admixture with, for example, an inert pharmaceutically acceptable carrier such as talc, starch, milk, sugar, or the like, or, alternatively, in the form of an aqueous solution, suspension, elixir or alcoholic solution in admixture with, for example, flavoring agents, colorants, thickeners or other conventional pharmaceutical excipients. Typically, these compositions are formulated to provide slow release of the active ingredient, that is, the compound of formula I, and specifically in the lower intestine.

Alternatively, the compound of formula I can be administered parenterally or rectally in corresponding dosage forms which include suitable excipients. Conventional methods of preparation known to those skilled in the art can be employed.

By way of further description, formulations for orally administrable compositions, rectally administrable compositions and parenteral compositions in accordance with this invention are provided among the examples that form part of this description.

The dose of a compound of formula I and the frequency of administration will depend on the severity of the condition, age of the subject being treated, and potency, duration and concentration of the particular compound being used as the active ingredient.

Doses contemplated for use in the practice of the invention are in the range from about 50 to about 4000 mg per day, and preferably from about 150 to about 500 mg, either as a single dose or in divided doses daily.

The useful anti-inflammatory activity of this invention is demonstrated in warm-blooded animals using standard pharmacological procedures. Exemplary of such procedures are:

A. Rat Colon Mucosa, In Vitro

The rat colon mucosa bioassay system is based on the measurement of changes in salt transport across the animal tissue due to absorption or secretion, using the standard short-circuit current technique described by Ussing, et al., Acta Physiol. Scand. 23: 110–127 (1951). Diarrhea is the most common symptom of gastrointestinal inflammation and is present in all types of inflammatory bowel disease. Pantera, et al., Ital. J. Gastroenterol. 13: 24–27 (1981); Sales, et al., Arch. Int. Med. 143: 294–299 (1983); Hodgson, Br. J. Clin. Pharmac. 14: 159–270 (1982). Diarrhea results from decreases in the salt absorption or increases in the salt secretion in the bowel and can be quantified in vitro by the above mentioned method of Ussing et al. In particular, a one-cm segment of colon is removed from animals weighing 200 to 250 g, exposed in vitro to leukotrienes or to bradykinin, which are inducers of salt secretion, and the resulting change in the net salt transport with and without the presence of 6-acetyl-7-[5-(4-acetyl-3-hydroxy-2-propylphenoxy) pentyloxy]-3,4-dihydro-2H-1-benzopyran-2-carboxylic acid as an inhibitor is measured. Tissues were mounted in pairs in Ussing chambers and short-circuited with automatic voltage clamps (from the University of Iowa Bioengineering Department). A 15-minute period of equilibrium was allowed for the preparation to reach steady state. Percent Inhibition calculations were made by comparing the response in paired tissues exposed to bradykinin (or to leukotrienes), on the one hand, and to bradykinin (or to leukotrienes) plus a given concentration of the inhibitor, on the other hand.

Bradykinin is used in this system because it is known to stimulate phospholipase $A_2$, which results in the production of leukotrienes, substance known to induce salt secretion in intestinal tissue in vitro. Musch, et al., J. Clin. Invest. 71: 1073–1083 (1983); Hojvat, et al., J. Pharmacol. Exp. Ther., 226: 749–755 (1983); Cuthbert, et al., Br. J. Pharmac. 82: 597–607 (1984); Musch, et al., Science 217: 1255–1256 (1982). The activity of bradykinin in the production of leukotrienes is suppressed by inhibitors of leukotriene biosynthesis; Cuthbert, et al., Br. J. Pharmac. 75: 587–598 (1982); Musch, et al., J. Clin. Invest., supra; Hojvat, et al., J. Pharmacol. Exp. Ther., supra.

The test results are set forth in Table 1 and in FIG. 1, which measure the ability of racemic 6-acetyl-7[5-(4-acetyl-3-hydroxy-2-propylphenoxy)pentyloxy]-3,4-dihydro-2H-1-benzopyran-2-carboxylic acid, (the test Inhibitor) in accordance with this invention, to reduce the secretory activity of leukotrienes (Table 1) and of bradykinin (FIG. 1).

TABLE 1

| Inhibitor Concentration, in micromolar ($\mu$M) | Effect of Inhibitor on Leukotriene - Induced Electrolyte Secretion by the Rat Colon (In Vitro) | | | |
|---|---|---|---|---|
| | % Inhibition Against Leukotrienes* | | | |
| | $LTB_4$ | $LTC_4$ | $LTD_4$ | $LTE_4$ |
| 1 | 44.4 ± 13.1 | 9.5 ± 19.2 | 30.8 ± 15.4 | 29.8 ± 15.0 |
| 10 | 69.6 ± 11.9 | 57.1 ± 19.7 | 62.4 ± 10.0 | 44.2 ± 9.8 |

LT = leukotriene
*Each value of % Inhibition based on six animals tested.

B. Antibiotic-Induced Colitis in Hamsters, In Vivo

Male Syrian hamsters (LUG), weighing 80 to 120 g, were each given a single dose of 175 mg/kg of clindamycin-phosphate or of clindamycin-hydrochloride intraperitoneally, to induce colitis. Approximately seven hours after injection, the animals were given the test compound orally or intraperitoneally and the therapy was continued twice a day for a period of four more days. For oral administration, the antibiotic was suspended in water or dissolved in dimethylsulfoxide and delivered to the animals by gavage using an oral intubating needle. The effect of the therapy was measured by use of the Hazard Ratio, which is the ratio of the mortality of the animals treated with the test inhibitor compound contained in a vehicle to the mortality of the animals treated with the vehicle containing none of the test inhibitor compound. The mortality was determined for the test inhibitor compound-treated groups and for the vehicle-treated groups, respectively, twice daily, and was evaluated by comparing the survival curves of each group. The Kaplan-Meier estimate of the survival curve was calculated for each group and the Mantel-Cox (logrank) test was used to compare the survival curve of each test inhibitor compound-treated (therapy) group to that of the corresponding vehicle control group. A Hazard Ratio of 1.0 indicates that the therapy has no better effect compared with the vehicle alone, while a Hazard Ratio greater than 1.0 (>1.0) indicates that the therapy prolongs survival in comparison with the group treated with the vehicle alone.

Racemic 6-acetyl-7-[5-(4-acetyl-3-hydroxy-2-propylphenoxy) pentyloxy]-3,4-dihydro-2H-1-benzopyran-2-carboxylic acid was found to be active when given orally at doses ranging from 10 to 100 mg/kg. Two known leukotriene inhibitors, namely 7-[3-(4-acetyl-3-hydroxy-2-propylphenoxy)-2-hydroxypropoxy]-4-oxo-8-propyl-4H-1-benzopyran-2-carboxylic acid (Comparison 1) and 7-[3-(4-acetyl-3-hydroxy-2-propylphenoxy)-propoxy]-4-oxo-8-propyl-4H-1-benzopyran-2-propanoic acid (Comparison 2), were inactive orally at 10 mg/kg (see Table 2).

In addition to prolonging the survival of the clindamycin-treated animals, racemic 6-acetyl-7-[5-(4-acetyl- 3-hydroxy-2-propylphenoxy)pentyloxy]-3,4-dihydro-2H-1-benzopyran-2-carboxylic acid reduced the diarrhea and substantially benefited the histopathology of the cecum and colon. In particular, the cecum of the clindamycin-treated hamsters was initially characterized by edema, extensive hemorrhaging and congestion, necrosis and focal erosions of the mucosa, as well as an increase in the infiltration of the mucosa by inflammatory cells. There were similar but less severe effects in the colon. In most cases these effects were reduced or abolished by the administration of 60 or of 100 mg/kg of the above compound.

TABLE 2

THERAPEUTIC ACTIVITY OF LEUKOTRIENE INHIBITORS AGAINST ANTIBIOTIC-INDUCED COLITIS (IN VIVO)

| Test Compound | Dose (mg/kg) | Hazard Ratio | 95% Confidence Interval | n |
|---|---|---|---|---|
| Racemic-6-acetyl-7-[5-(4-acetyl-3-hydroxy-2-propyl-phenoxy)pentyloxy]-3,4-dihydro-2H-1-benzopyran-2-carboxylic acid | $10^a$ | 2.87 | 2.00–4.13 | 20 |
| | $60^a$ | 4.77 | 3.05–7.45 | 20 |
| | $10^b$ | 3.80 | 2.64–5.46 | 25 |
| | $60^b$ | 12.0 | 7.30–19.8 | 20 |
| | $100^b$ | 64.2 | 22.5–183 | 20 |
| Comparison 1 | $10^a$ | $2.02^c$ | 1.43–2.85 | 20 |
| | $10^b$ | 1.42 | 1.07–1.89 | 25 |
| Comparison 2 | $13^b$ | 1.68 | 1.25–2.27 | 25 |

$^a$Intraperitoneal administration, in 0.075 ml PEG-400
$^b$Oral administration, in 0.15 ml water
$^c p < 0.05$ vs. vehicle by Mantel-Cox and Global Chi Square Tests
$^d p < 0.01$ vs. vehicle by Mantel-Cox and Global Chi Square Tests
n = number of animals tested C. Acetic Acid-Induced Colitis in Rats, In Vivo The rat acetic acid-induced colitis bioassay has been described by J. E. Krawisz, et al. in Amer. J. Proc. Gastro. Col. Rec. Surg. 31: 11–18 (1980), and by P. Sharon and W. F. Stenson in Gastroenterology 88: 55–63 (1985) and 86: 453–460 (1984). Acetic acid-induced colitis is characterized by the movement of inflammatory cells into the colon, with the number of such cells in the mucosa being measured by the activity of myeloperoxidase, a marker enzyme for these cells. Positive desirable activity is indicated by a reduction in the high levels of myeloperoxidase caused by acetic acid. Male rats (Sprague-Dawley), weighing 150 to 300 g, were pretreated twice daily for two days with either the vehicle (water, or dimethylsulfoxide) or the test inhibitor compound suspended in water or dissolved in dimethylsulfoxide and orally administered. On the third day, the animals were dosed the same as on the previous two days, anesthetized with metofane, and 2 ml of 2.5% acetic acid was injected by syringe into the colonic lumen, followed immediately by 3 ml of air and a rinse consisting of 3 ml of phosphate-buffered saline (the acetic acid is present in the lumen for a sufficient period to cause inflammation without producing severe necrosis or irreversible damage). The animals were administered a second dose of the test compound in the same amount about 16 hours later. Twenty four hours after the acetic acid treatment, the animals were sacrificed, the colonic mucosa was surgically removed and homogenized in an aqueous buffer at pH 6 with a Tissumizer or similar device, and myeloperoxidase was measured in the homogenate using o-phenylenediamine as a chromagen, as described by A. Voller, D. E. Bidwell and A. Bartlett in The Enzyme Linked Immunosorbent Assay (ELISA), Zoological Soc., London, 1979, pages 29–30. Control animals were pretreated with the vehicle and saline in place of acetic acid.

Figure 2:
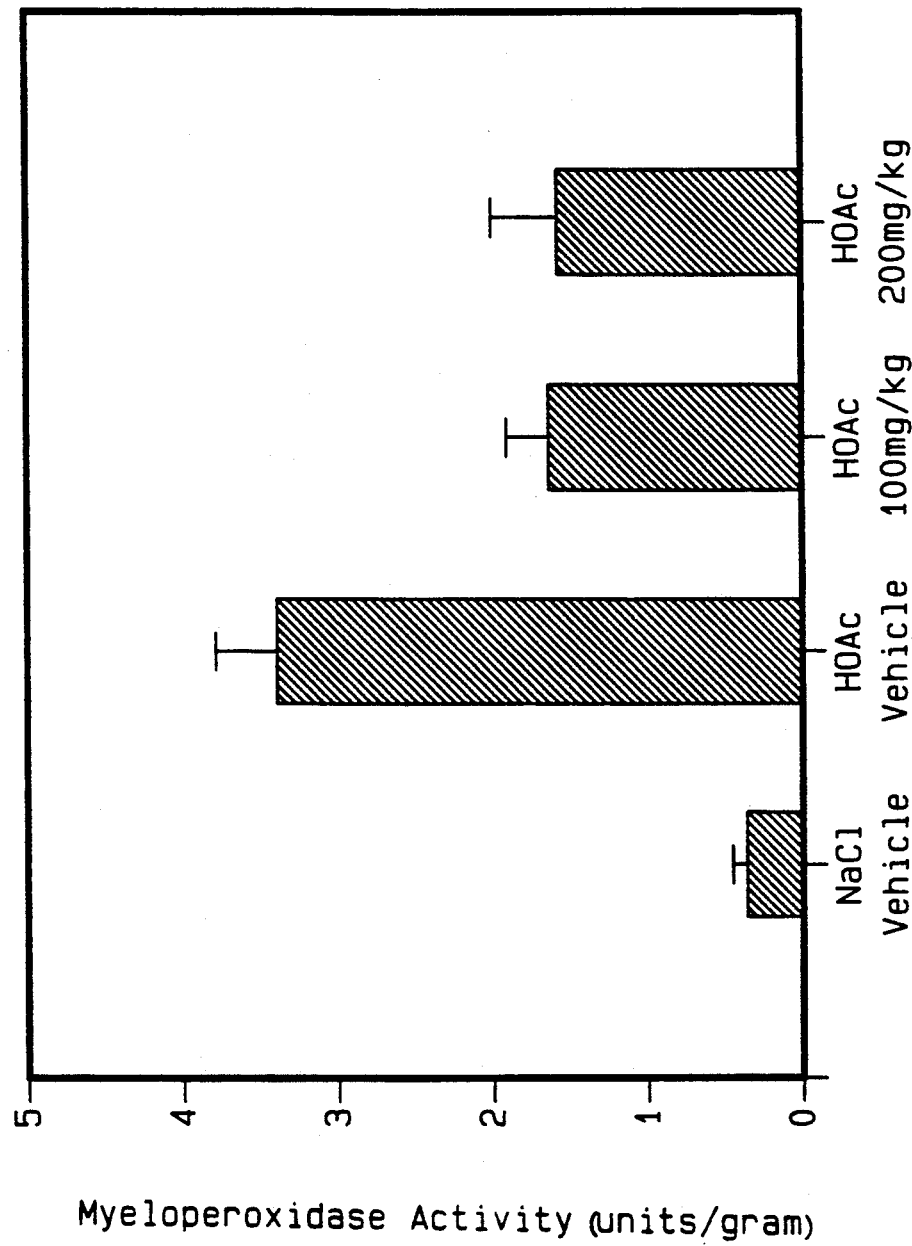
FIG. 2—Effect of phenidone on myeloperoxidase of the rat colon, in vivo.
Figure 3:
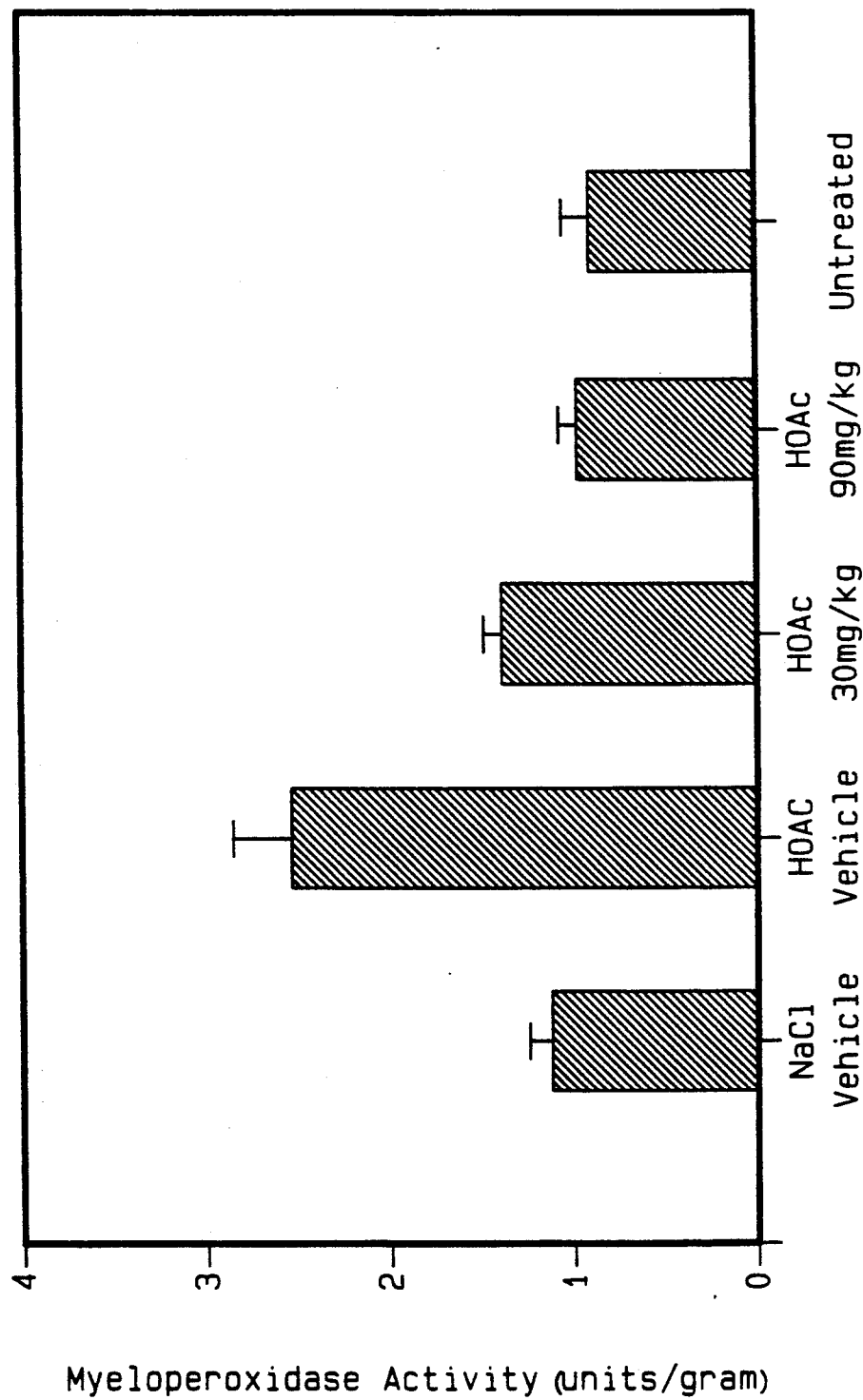
FIG. 3—Effect of test inhibitor on myeloperoxidase of the rat colon, in vivo.

Using the test procedure described above, racemic-6-acetyl-7-[5-(4-acetyl-3-hydroxy-2-propylphenoxy)pentyloxy]-3,4-dihydro-2H-1-benzopyran-2-carboxylic acid was compared with phenidone, a known leukotriene synthesis inhibitor. The results shown in FIGS. 2 and 3 were obtained. As seen, phenidone was active when given orally at 100 and 200 mg/kg (FIG. 2), while racemic-6-acetyl-7[5-(4-acetyl-3-hydroxy-2-propylphenoxy)pentyloxy]-3,4-dihydro-2H-1-benzopyran-2-carboxylic acid was active when given orally at the even smaller doses of 30 and 90 mg/kg (FIG. 3).

D. Carrageenan-Induced Colitis in Guinea Pigs, In Vivo

The guinea pig carrageenan-induced colitis bioassay has been described by A. B. Onderdonk in Inflammatory Bowel Diseases, Martinus Nijhoff Publ., Boston, Mass., pages 126–134 (1982), and in Human Intestinal Microflora in Health and Disease (D. J. Hentger, ed.), Academic Press, New York, 1983, pages 447–479. The polysaccharide iotacarrageenan, derived from red seaweed, produces a colitis in guinea pigs that resembles ulcerative colitis in humans. Male/female guinea pigs (Hartley), weighing 400 to 650 g, were given a 3% solution of degraded carrageenan in their drinking water on a daily basis. After about 7 days, the animals began to develop diarrhea, ceased to gain weight and became lethargic. After the animals received carrageenan in this manner for 14 days, the diarrhea was quantified by measuring the water transport in the distal colon by single pass perfusion using 14C-polyethylene glycol 4000 (PEG 4000) as a marker. Control animals were given an aqueous drinking solution containing 3% mannitol in place of the carrageenan. Simultaneously, randomly selected animals from each of these two groups were treated orally with the test inhibitor compound, twice daily.

Comparison was made between racemic-6-acetyl-7-[5-(4-acetyl-3-hydroxy-2-propylphenoxy)pentyloxy]-3,4-dihydro-2H-1-benzopyran-2-carboxylic acid, in accordance with this invention, and sulfasalazine, a standard in this system, as the test inhibitor compounds. The results are reported in FIGS. 4 and 5.

As can be seen, sulfasalazine at an oral dose of 100 mg/kg restored the water transport in the colon of the diseased animals from a net secretory level to a level about that of the control animals (FIG. 4). Animals medicated with racemic-6-acetyl-7-[5-(4-acetyl-3-hydroxy-2-propylphenoxy)pentyloxy]-3,4-dihydro-2H-1-benzopyran-2-carboxylic acid, on the other hand, at lower oral doses of 10 and 30 mg/kg, respectively, had water transport rates about equal to that of the control animals (FIG. 5).

EXAMPLE 1

| Oral Formulation* (Tablet) | |
|---|---|
| Ingredients | mg/tablet |
| racemic-6-acetyl-7-[5-(4-acetyl-3-hydroxy-2-propylphenoxy)pentyloxy]-3,4-dihydro-2H-1-benzopyran-2-carboxylic acid | 250.0 mg |
| lactose | 50.0 mg |

-continued

| Oral Formulation (Tablet) | |
|---|---|
| Ingredients | mg/tablet |
| starch | 25.0 mg |
| polyvinyl pyrrolidone | 2.5 mg |
| magnesium stearate | 2.5 mg |
| Total weight | 330.0 mg |

Procedure:

Granulate a mixture of the powdered ingredients with the polyvinyl pyrrolidine in solution and press into a tablet. Then coat the table by spraying coating or by rotating the tablet in a coating pan with the following coating solution:

| | Wt % |
|---|---|
| hydroxypropyl methylcellulose-phthalate | 6 |
| alcohol 3A | 47 |
| methylene chloride | 47 |
| Total Weight | 100% |

The resulting coated tablets are resistant to gastric fluid but dissolve in intestinal fluid, when tested by the USP in-vitro dissolution test.

EXAMPLE 2

| Oral Formulation (Soft gelatin capsule) | |
|---|---|
| Ingredients | mg/tablet |
| sodium salt of racemic-6-acetyl-7-[5-(4-acetyl-3-hydroxy-2-propylphenoxy)pentyloxy]-3,4-dihydro-2H-1-benzopyran-2-carboxylic acid | 261.0* mg |
| triglycerides (medium chain length) | 229.0 mg |
| sodium silicates | 10.0 mg |
| Total Weight | 500.00 mg |

*Equivalent to 250 mg of free acid

Procedure:

The ingredients are formed into a suspension and loaded into a soft gelatin capsule. The capsule is coated to make it resistant to gastric fluid but dissolves in intestinal fluid when tested by the USP in-vitro dissolution test.

EXAMPLE 3

| Oral Formulation (Beadlets) | |
|---|---|
| Ingredients | mg/dose |
| racemic-6-acetyl-7-[5-(4-acetyl-3-hydroxy-2-propylphenoxy)pentyloxy]-3,4-dihydro-2H-1-benzopyran-2-carboxylic acid | 250 mg |
| polyvinyl pyrrolidine | 25 mg |
| starch | 50 mg |
| Total Weight | 325 mg |

Procedure:

The beadlets are prepared by wet granulation and then coated with the below polymeric solution by spraying on the surface of the beadlets in a rotating coating pan.

| | wt. % |
|---|---|
| polymethacrylic acid polymer | 5.0 |
| ethyl cellulose | 1.0 |
| acetone | 10.0 |
| isopropyl alcohol | 84.0 |
| Total Weight | 100.0% |

The coated beadlets are resistant to gastric fluid but dissolve in intestinal fluid when tested by the USP in-vitro dissolution test.

EXAMPLE 4

| Oral Formulation (Tablet) | | |
|---|---|---|
| | mg/tablet | |
| Ingredients | 100 mg | 600 mg |
| racemic-6-acetyl-7-[5-(4-acetyl-3-hydroxy-2-propylphenoxy)pentyloxy]-3,4-dihydro-2H-1-benzopyran-2-carboxylic acid | 100 mg | 600 mg |
| lactose | 30 mg | 100 mg |
| pregelatinized starch | 4 mg | 25 mg |
| microcrystalline cellulose | 20 mg | 120 mg |
| modified starch | 5 mg | 25 mg |
| magnesium stearate | 1 mg | 8 mg |
| Total Weight | 160 mg | 878 mg |

Procedure:

Racemic racemic-6-acetyl-7-[5-(4-acetyl-3-hydroxy-2-propylphenoxy)pentyloxy]-3,4-dihydro-2H-1-benzopyran-2-carboxylic acid, lactose, pregelatinized starch and microcrystalline cellulose are mixed together and granulated in water, the granulated material is dried at 45°–50° C. and milled, the modified starch and magnesium stearate are added, and the resulting granulation mixture is tabletted in a press.

EXAMPLE 5

| Oral Formulation (Tablet) | | |
|---|---|---|
| | mg/tablet | |
| Ingredients | 100 mg | 600 mg |
| racemic-6-acetyl-7-[5-(4-acetyl-3-hydroxy-2-propylphenoxy)pentyloxy]-3,4-dihydro-2H-1-benzopyran-2-carboxylic acid | 100 mg | 600 mg |
| lactose | 40 mg | 200 mg |
| polyvinylpyrrolidone | 4 mg | 24 mg |
| modified starch | 4 mg | 24 mg |
| magnesium stearate | 1 mg | 6 mg |
| Total Weight | 149 mg | 856 mg |

Procedure:

Racemic 6-acetyl-7-[5-(4-acetyl-3-hydroxy-2-propylphenoxy)pentyloxy]-3,4-dihydro-2H-1-benzopyran-2-carboxylic acid, lactose and modified starch are mixed together and granulated with polyvinylpyrrolidone in water or alcohol, the granulated material is dried at 45°–50° C. and milled, the magnesium stearate is added, and the resulting granulation mixture is tabletted on a press.

EXAMPLE 6

| Oral Formulation (Capsule) | | |
|---|---|---|
| | mg/tablet | |
| Ingredients | 100 mg | 600 mg |
| racemic-6-acetyl-7-[5-(4-acetyl-3-hydroxy-2-propylphenoxy)pentyloxy]-3,4-dihydro-2H-1-benzopyran-2-carboxylic acid | 100 mg | 600 mg |
| lactose* | 50 mg | — |
| pregelatinized starch** | 5 mg | 30 mg |
| talc | 4 mg | 24 mg |
| magnesium stearate | 1 mg | 6 mg |
| Total Weight | 160 mg | 660 mg |

*Can be substituted by dicalcium phosphate dihydrate, mannitol or sorbitol
**Can be substituted by hydroxypropylmethylcellulose, gelatin or silicates Procedure:

Racemic 6-acetyl-7-[5-(4-acetyl-3-hydroxy-2-propylphenoxy)pentyloxy]-3,4-dihydro-2H-1-benzopyran-2-carboxylic acid, lactose and pregelatinized starch are mixed together and granulated in water, the granulated material is dried at 45°-50° C. and milled, the talc and magnesium stearate are added, and the resulting mixture is poured into a soft gelatin or liquid capsule.

EXAMPLE 7

| Parenteral Formulation | |
|---|---|
| Ingredients | mg/tablet |
| racemic-6-acetyl-7-[5-(4-acetyl-3-hydroxy-2-propylphenoxy)pentyloxy]-3,4-dihydro-2H-1-benzopyran-2-carboxylic acid | 10 mg |
| mannitol* | 20 mg |
| sodium hydroxide and/or hydrochloric acid to adjust pH | q.s. |
| water (for injection), q.s. to make | 1.0 ml |
| Total Volume | 1.0 ml |

*Can be substituted by lactose

Procedure:

Racemic 6-acetyl-7-[5-(4-acetyl-3-hydroxy-2-propylphenoxy)pentyloxy]-3,4-dihydro-2H-1-benzopyran-2-carboxylic acid and mannitol are dissolved in the water and the pH is adjusted. The solution is then lyophilized in a suitable container (removing the water).

EXAMPLE 8

| Parenteral Formulation | |
|---|---|
| Ingredients | Percent by Weight |
| racemic-6-acetyl-7-[5-(4-acetyl-3-hydroxy-2-propylphenoxy)pentyloxy]-3,4-dihydro-2H-1-benzopyran-2-carboxylic acid | 1.0% |
| benzyl alcohol* | 1.0% |
| propylene glycol** | 10.0% |
| emulphor** | 5.0% |
| phosphate buffer, q.s. to pH | 7.5 |
| water (for injection), q.s. to make | 100% |

*Can be substituted by thimerosal, phenol, methyl and propyl parabens, benzothonium chloride, or chlorobutanol
**Can be substituted by polyethylene glycols, alcohol, dimethylacetamide, glycerine, povidone, lecithin, sorbitan monooleate and trioleate Procedure:

The phosphate buffer is dissolved in a portion of the water, the benzyl alcohol, propylene glycol and emulphor are added with stirring in the buffered soluton, racemic 6-acetyl-7-[5-(4-acetyl-3-hydroxy-2-propylphenoxy)pentyloxy]-3,4-dihydro-2H-1-benzopyran-2-carboxylic acid is dissolved in the solution, the pH is adjusted and water is added to the required amount, and the resulting solution is filled into a suitable container.

EXAMPLE 9

| Rectal Formulation (Suppository) | | |
|---|---|---|
| | mg/suppository | |
| Ingredients | 100 mg | 1000 mg |
| racemic-6-acetyl-7-[5-(4-acetyl-3-hydroxy-2-propylphenoxy)pentyloxy]-3,4-dihydro-2H-1-benzopyran-2-carboxylic acid | 100 mg | 1000 mg |
| suppository base*, q.s. to make | 1000 mg | 2000 mg |
| Total Weight | 1000 mg | 2000 mg |

*Contains semi-synthetic glycerides, blend of triglycerides such as Witepsol H15 of Dynamit Nobel Chemicals, and polyethylene glycols 400 and 4000, individually or in combination as desired Procedure:

The racemic 6-acetyl-7-[5-(4-acetyl-3-hydroxy-2-propylphenoxy)pentyloxy]-3,4-dihydro-2H-1-benzopyran-2-carboxylic acid is dispersed in the molten suppository base and the resulting mass is filled into a suppository shell and sealed.

EXAMPLE 10

| Rectal Formulation (Suppository) | | |
|---|---|---|
| | mg/suppository | |
| Ingredients | 100 mg | 1000 mg |
| racemic-6-acetyl-7-[5-(4-acetyl-3-hydroxy-2-propylphenoxy)pentyloxy]-3,4-dihydro-2H-1-benzopyran-2-carboxylic acid | 100 mg | 1000 mg |
| sorbitan trioleate | 100 mg | 600 mg |
| cocoa butter, q.s. to make | 1000 mg | 2000 mg |
| Total Weight | 1000 mg | 2000 mg |

Procedure:

The cocoa butter is melted and the sodium salt of racemic 6-acetyl-7-[5-(4-acetyl-3-hydroxy-2-propylphenoxy)pentyloxy]-3,4-dihydro-2H-1-benzopyran-2-carboxylic acid and sorbitan trioleate are dispersed in it, and the mass is filled into a suppository shell and sealed.

EXAMPLE 11

| Rectal Formulation (Enema) | | |
|---|---|---|
| | amt./enema | |
| Ingredients | 100 mg | 1000 mg |
| sodium salt of racemic-6-acetyl-7-[5-(4-acetyl-3-hydroxy-2-propylphenoxy)pentyloxy]-3,4-dihydro-2H-1-benzopyran-2-carboxylic acid | 100 mg | 1000 mg |
| polyethylene glycol 400 | 10 ml | 15 ml |
| water for injection, q.s. to make | 120 ml | 180 ml |
| Total Volume | 120 ml | 180 ml |

Procedure:

The sodium salt of racemic-6-acetyl-7-[5-(4-acetyl-3-hydroxy-2-propylphenoxy)pentyloxy]-3,4-dihydro-2H-1-benzopyran-2-carboxylic acid and polyethylene glycol 400 are premixed and dissolved in the water for injection, and the solution is loaded into an appropriate squeezable plastic container from which it can be dispensed.

We claim:

1. A method for treating inflammatory bowel disease by inhibiting leukotriene-mediated inflammation in the intestine, which comprises administering to a host requiring such treatment an effective anti-inflammatory leukotriene-inhibiting amount of a compound of the formula

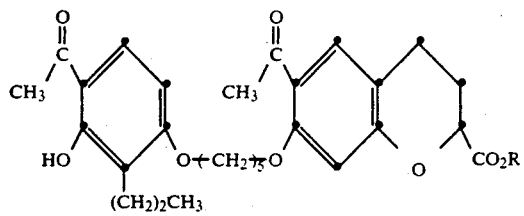

in which R is hydrogen or lower alkyl, or a salt thereof where R is hydrogen, or an enantiomer thereof.

2. The method of claim 1, in which R is hydrogen.

3. The method of claim 1, in which R is lower alkyl.

4. The method of claim 1, in which the compound is racemic-6-acetyl-7-[5-(4-acetyl-3-hydroxy-2-propylphenoxy)pentyloxy]-3,4-dihydro-2H-1-benzopyran-2-carboxylic acid.

5. The method of claim 1, comprising the use of a daily total dose in the range from about 50 to about 4000 mg.

6. The method of claim 1, comprising the use of a daily total dose in the range from about 150 to about 500 mg of the compound.

7. The method of claim 1, comprising oral administration.

8. The method of claim 1, comprising rectal administration.

9. The method of claim 1, comprising parenteral administration.

10. The method of claim 1, which is used to treat mucosal inflammation of the small and large intestine.

11. A method for treating inflammatory bowel disease which comprises administering to a host requiring such treatment an effective anti-flammatory amount of a compound of the formula

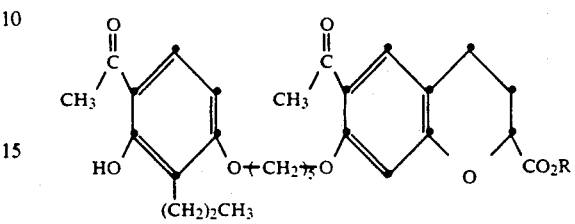

in which R is hydrogen or lower alkyl, or a salt thereof where R is hydrogen, or an enantiomer thereof.

12. The method of claim 11, in which R is hydrogen.

13. The method of claim 11, in which R is lower alkyl.

14. The method of claim 11, in which the compound is racemic-6-acetyl-7-[5-(4-acetyl-3-hydroxy-2-propylphenoxy)pentyloxy]-3,4-dihydro-2H-1-benzopyran-2-carboxylic acid.

15. The method of claim 11, comprising the use of a daily total dose in the range from about 50 to about 4000 mg.

16. The method of claim 11, comprising the use of a daily total dose in the range from about 150 to about 500 mg of the compound.

17. The method of claim 11, comprising oral administration.

18. The method of claim 11, comprising rectal administration.

19. The method of claim 11, comprising parenteral administration.

* * * * *